United States Patent
Windhorst et al.

(10) Patent No.: US 8,445,733 B1
(45) Date of Patent: May 21, 2013

(54) 1,3 BUTYLENE GLYCOL WITH REDUCED ODOR

(75) Inventors: Kenneth A. Windhorst, Portland, TX (US); Oakley Cortez, Corpus Christi, TX (US)

(73) Assignee: Oxea Bishop LLC, Dallas, TX (US)

( * ) Notice: Subject to any disclaimer, the term of this patent is extended or adjusted under 35 U.S.C. 154(b) by 0 days.

(21) Appl. No.: 13/523,001

(22) Filed: Jun. 14, 2012

Related U.S. Application Data

(60) Provisional application No. 61/572,986, filed on Jul. 26, 2011.

(51) Int. Cl.
*C07C 29/74* (2006.01)
*C07C 29/76* (2006.01)

(52) U.S. Cl.
USPC .......................... 568/870; 568/868; 568/869

(58) Field of Classification Search
USPC .......................................... 568/868, 869, 870
See application file for complete search history.

(56) References Cited

U.S. PATENT DOCUMENTS

| | | | |
|---|---|---|---|
| 5,345,004 A | 9/1994 | Nishiguchi | 568/865 |
| 5,583,270 A | 12/1996 | Nishiguchi | 568/865 |
| 6,376,725 B1 | 4/2002 | Tsuji et al. | 568/868 |
| 6,900,360 B2 | 5/2005 | Tsuji et al. | 568/852 |
| 2004/0254407 A1 | 12/2004 | Mizutani et al. | 568/852 |

FOREIGN PATENT DOCUMENTS

| | | |
|---|---|---|
| JP | 61-065834 | 4/1986 |
| JP | 04-217637 | 8/1992 |
| JP | 7258129 | 10/1995 |
| JP | 2003-252811 | 9/2003 |
| WO | WO 2005/068408 | 7/2005 |

OTHER PUBLICATIONS

Kirk Othmer Encyclopedia of Chemical Technology, 3rd Ed., vol. 4, pp. 561-569; Material Safety Data Sheet: Calgon Carbon Corporation; Product Type: F200 GLY; Product Code: 1965; Material Safety. Datasheet: Jacobi Carbons AB; Product Name: ColorSorb®; Chemical Name: Activated Carbon; Chemical Family: Carbon; Formula: C; CAS No. 7440-44-0.
Material Safety Data Sheet: MeadWestvaco; Product Name: NUCHAR® WV-B; Material uses: water purification, multi-gas/vapor filter; Product Data Bulletin: MeadWestvaco; Product Name: NUCHAR® WV-B; Product Data Bulletin: MeadWestvaco; Product Name: AQUA NUCHAR®.
Product Data Bulletin: MeadWestvaco; Product Name: NUCHAR® MWC; Product Data Bulletin: MeadWestvaco; Product Name: NUCHAR® BX-7530; Product Data Bulletin: MeadWestvaco; Product Name: NUCHAR® BX-7540; MeadWestvaco Specialty Chemicals Technical Sheet; Product Name: MWV NUCHAR® Powdered Carbons.
Environmental Working Group (2011) Butylene Glycol Skin Deep Cosmetics Database; Chemical Book (2010: Chemical Name: Diglycerol; CAS No. 627-82-7; and Wikipedia: Activated Carbon definition.

*Primary Examiner* — Elvis O Price
(74) *Attorney, Agent, or Firm* — Michael W. Ferrell

(57) ABSTRACT

A method of reducing odor of 1,3-butylene glycol includes contacting the 1,3-butylene glycol with an activated carbon selected from wood-based activated carbons and chemically activated carbons.

20 Claims, 2 Drawing Sheets

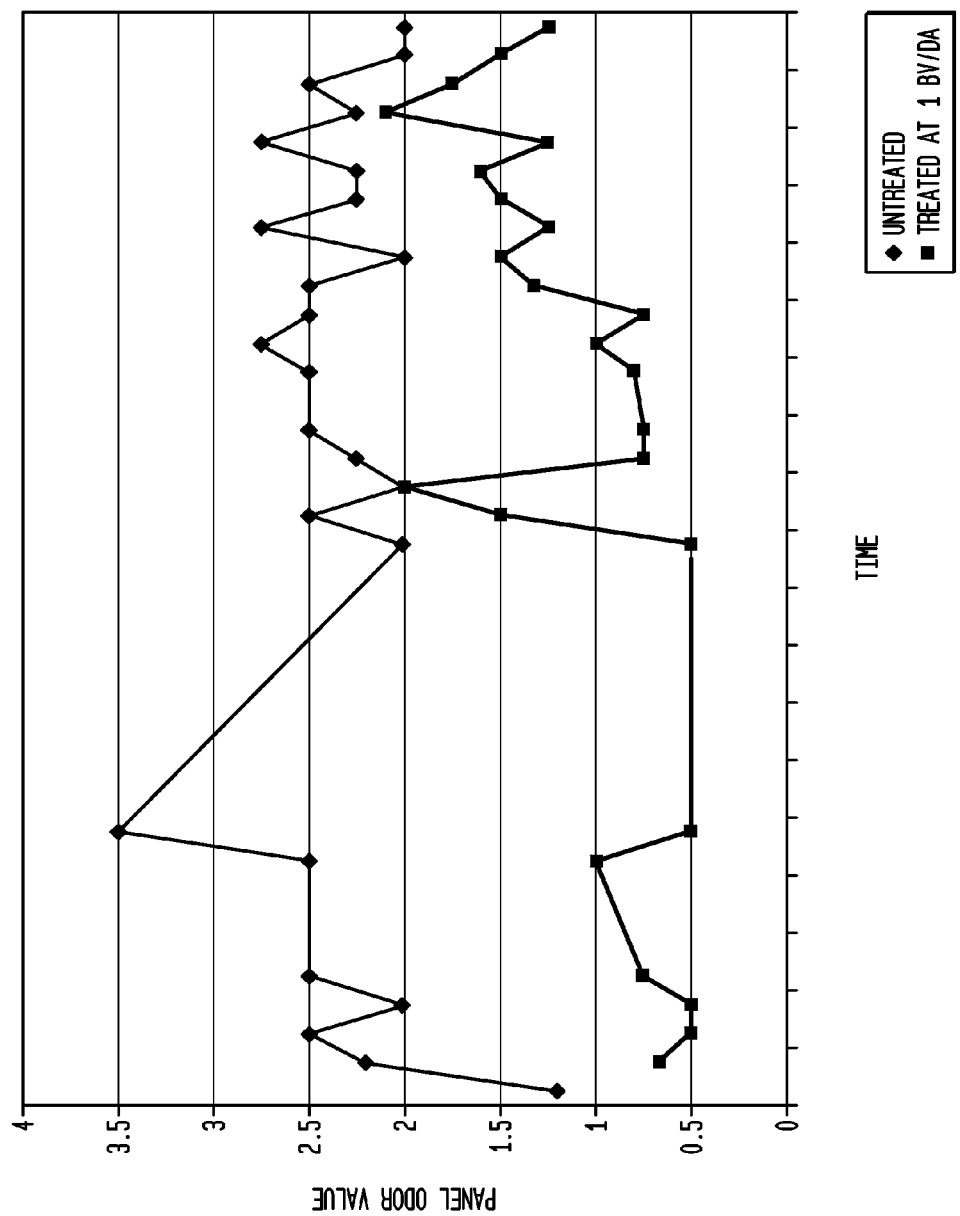

1,3 BUTYLENE GLYCOL WITH REDUCED ODOR

CLAIM FOR PRIORITY

This application is based on U.S. Provisional Patent Application Ser. No. 61/572,986 of the same title, filed Jul. 26, 2011, the priority of which is hereby claimed and the disclosure of which is incorporated herein by reference.

TECHNICAL FIELD

The present invention relates to 1,3-butylene glycol with reduced odor suitable for use in cosmetics and other products.

BACKGROUND 1,3-butylene glycol is conventionally manufactured by alcohol condensation of acetaldehyde to yield acetaldol which is then hydrogenated to 1,3-butylene glycol as described in WO 2005/068408. There are various processes recognized for producing 1,3-butylene glycol commercially. U.S. Pat. No. 6,376,725 discloses a process for producing 1,3-butylene gycol through a liquid phase hydrogenation of acetaldol (3-hydroxybutanal or aldol) in the presence of a Raney nickel catalyst. Acetaldol is commonly produced through the aldol condensation of two molecules of acetaldehyde. U.S. Pat. Nos. 5,345,004 and 5,583,270 disclose producing 1,3-butylene glycol in three-step processes including an aldol condensation of acetataldehyde to aldoxane, followed by decomposition of the aldoxane to obtain paraldol which is in turn hydrogenated to produce 1,3-butylene gycol.

Because the odor and odor stability over time is an important aspect of the product, various methods to remove odor causing impurities have been suggested in the art.

U.S. Pat. No. 6,900,360 to Tsuji et al. describes methods of preparing purified 1,3-butylene glycol from acetaldehyde. Acetaldehyde is condensed and the acetaldols are then converted to 1,3 butylene glycol. Chemical treatment with alkaline or acidic reagents or with ozone is used along with distillation to provide purified product.

U.S. Pat. No. 6,376,725 also to Tsuji et al. discloses 1,3-butylene glycol obtained from acetaldol by a liquid phase hydrogen reduction method, by adding a base to crude 1,3-butylene glycol free of high-boiling material, heat-treating the mixture and then distilling off 1,3-butylene glycol; and distilling off low-boiling materials from 1,3-butylene glycol.

A very similar process is described in JP 7258129 wherein a process to distill and purify 1,3-butylene glycol from a reaction mixture obtained by liquid phase reduction of acetaldol with hydrogen, at least one compound selected from sodium hydroxide, potassium hydroxide, sodium borohydride and potassium borohydride is added to the process to remove the high-boiling impurities contained in the original crude 1,3-butylene glycol.

United States Patent Application Publication No. US 2004/0254407 teaches to extract impurities from 1,3-butylene glycol by mixing the glycol with water and an organic solvent and to recover 1,3-butylene glycol from the aqueous phase by distillation or dehydration.

JP 61-065834 teaches to remove impurities from 1,3-butylene glycol by carrying out continuous distillation of 1,3-butylene glycol under reduced pressure with a thin-film evaporator while adding water to the system.

JP 2003252811 teaches to treat 1,3-butylene glycol with a non-ionic porous resin of styrene and divinyl benzene to remove impurities.

While various methods have been proposed to purify 1,3-butylene glycol, it is seen from the foregoing references that such processes are either complex or require specialized and expensive materials as is a process for purifying diglycerol (apparently to remove acroleins) by treatment with activated carbon followed by distillation described in JP 04217637.

In accordance with the present invention, 1,3-butylene glycol with reduced or no odor is obtained by treating conventionally produced 1,3-butylene glycol with certain activated carbons.

Activated carbons are readily available and may be purchased in the form of powders, granules or extruded pellets. Activated carbon is microcrystalline, non-graphitic form of carbon which has been processed to develop internal porosity. Almost any carbonaceous material of animal, plant or mineral origin can be converted to activated carbon if properly treated. Coal, hardwood or softwood sawdust or coconut shells, for example, can be used as the starting material. Activated carbons are further characterized by surface area, density and method of activation. Compounds used to chemically activate carbon are alkali metal hydroxides, carbonates, sulfides, sulfates; alkaline earth carbonates, chlorides, sulfates and phosphates; zinc chloride; sulfuric acid and phosphoric acid.

Alternatively, carbon may be activated by selective oxidation by treatment with steam, carbon dioxide or flue gas. Further details are described in *Kirk-Othmer Encyclopedia of Chemical Technology*, $3^{rd}$ Ed., Vol. 4, pp. 561-569, the disclosure of which is incorporated herein by reference.

SUMMARY OF INVENTION

Treatment of 1,3-butylene glycol with certain activated carbons is surprisingly effective in reducing odor. An especially preferred material is wood-based activated carbon which is believed chemically activated with phosphoric acid. This material is provided in granular form and has relatively low apparent density.

Further details and advantages will become apparent from the discussion which follows.

DESCRIPTION OF DRAWING

The invention is described in detail below with reference to the Figures, Wherein:

FIG. 2 is a plot of panel odor value versus time for 1,3-butylene glycol treated in the apparatus of FIG. 1.

DETAILED DESCRIPTION

Figure 1:
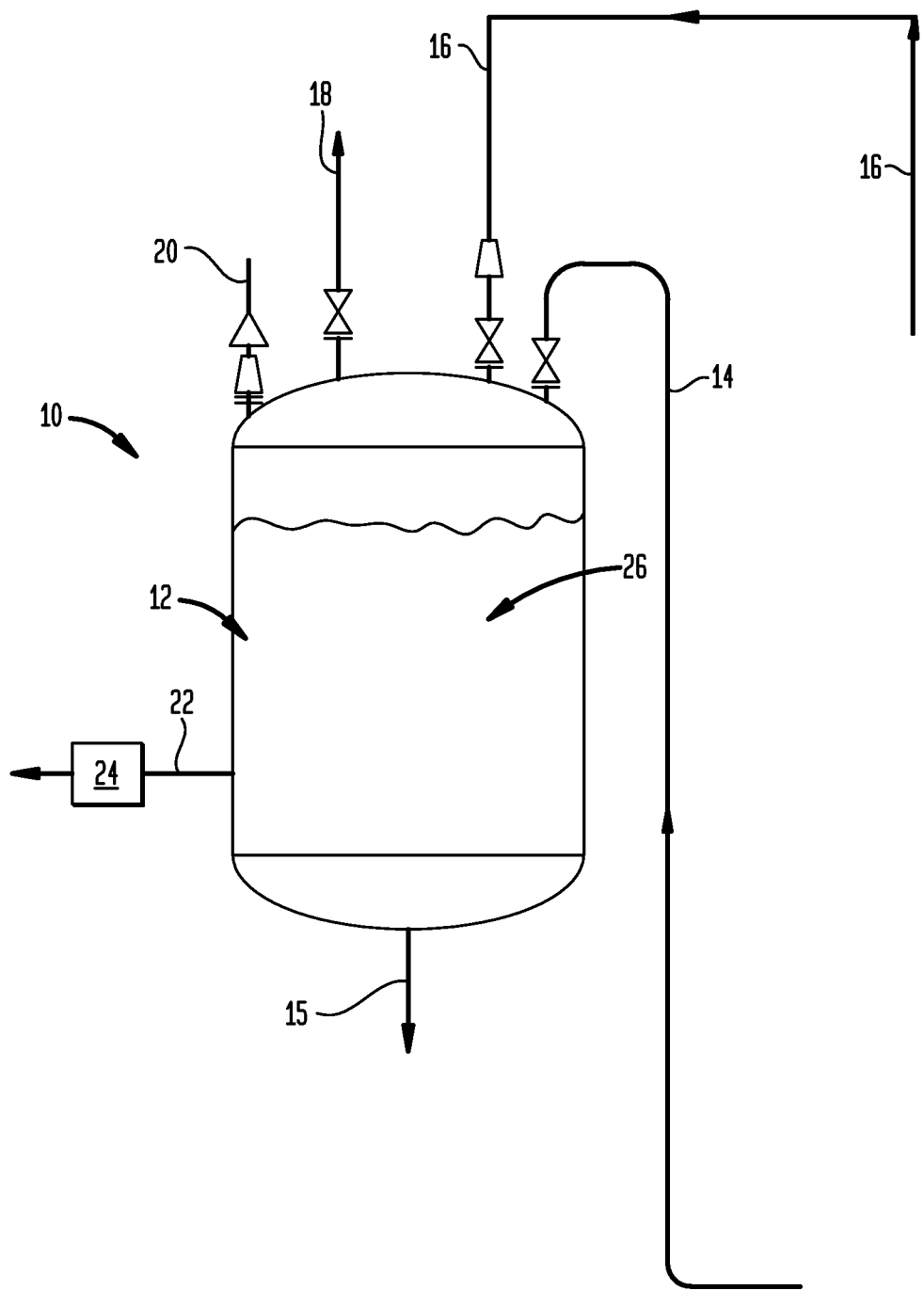
FIG. 1 is a schematic diagram illustrating operation of a bed of granular activated carbon used to reduce odor of 1,3-butylene glycol.

The invention is described in detail below with reference to the Figures and examples. Such discussion is for purposes of illustration only. Modifications to examples within the spirit and scope of the present invention, set forth in the appended claims will be readily apparent to one of skill in the art. Terminology used herein is given its ordinary meaning as supplemented or explained below. Unless otherwise indicated, a Test Method number refers to the version in effect as of May 1, 2011.

Apparent density of the activated carbon is measured in accordance with Test Method ASTM D 2854.

Bed turnovers by volume refers to the volume of material treated by a bed of activated carbon before the activated carbon is exhausted. Thus if a 100 liter bed treated 25,000 liters of product before the activated carbon was exhausted, 250 bed turnovers by volume were achieved before exhaustion.

"Chemically activated" and like terminology refers to activated carbon which has been activated by treatment with a chemical as opposed to oxidized with air or other gasses. Chemically activated carbon can be given a second activation with steam to impart physical properties not developed by chemical activation. Chemical activating agents which may be employed include phosphoric acid; sulfuric acid; zinc chloride; potassium sulfide; potassium thiocyanate; alkali metal hydroxides, carbonates; sulfides and sulfates; as well as alkaline earth carbonates; chlorides; sulfates; and phosphates.

A 1,3-butylene glycol treated with activated carbon is "consumed" without further purification when furnished to a customer and/or incorporated into another composition immediately after activated carbon treatment; that is, without further subsequent purification steps such as distillation and so forth.

"Iodine number" is measured in accordance with Test Method ASTM D 4607 and expressed in mg/g.

As used herein, the residence time of 1,3-butylene glycol in a bed of activated carbon is the bulk volume of activated carbon in the bed divided by the volumetric flow rate of 1,3-butylene glycol through the bed at steady state operation. Thus, 1,3-butylene glycol being treated in a 5,000 gallon bed at a flow rate of 10,000 gallons per day has a residence time of 12 hours.

Particularly useful activated carbon materials for use in connection with the present invention is distributed by MeadWestvaco Corporation as Nuchar® WV-B grade which has the characteristics set forth in Table I:

TABLE I

Activated Carbon Characteristics

| Specifications | WV-B 20 | WV-B 30 |
|---|---|---|
| Iodine Number, (mg/g) | 900 min | 900 min |
| Moisture, (% As Packed) | 10 max | 10 max |
| Particle Size | | |
| Nominal (US Mesh) | 6 × 18 | 8 × 25 |
| Oversize (%) | 8 max | 8 max |
| Undersize (%) | 5 max | 5 max |
| Apparent Density, (lbs/cu ft) | 15-19 | 15-19 |
| Apparent Density, (kg/m$^3$) | 240-300 | 240-300 |
| Surface Area, [Nitrogen BET Method] (m$^2$/g) | 1400-1600 | 1400-1600 |

These materials are believed to be wood-based (sawdust) activated carbons, activated with phosphoric acid. Without intending to be bound by theory, it is believed that the activation and/or pore structure of these materials accounts for its superior ability to remove odor-causing bodies from 1,3-butylene glycol.

The nature of odor-causing bodies in 1,3-butylene glycol is not well understood. A series of preliminary experiments were carried out by mixing the additives enumerated in Table II with commercial 1,3-butylene glycol.

TABLE II

Additive Testing

| Additive | Result |
|---|---|
| Potassium Hydroxide | No change |
| Potassium Permanganate | Increased Odor |

TABLE II-continued

Additive Testing

| Additive | Result |
|---|---|
| Phosphoric Acid | Slightly Better |
| Sodium Borohydride | Slightly Better |
| Potassium Dichromate | Increased Odor |
| Activated Carbon | Unanimously, Significantly Better |
| Compressed Air | Slightly Better |

Based on the results from this study, the functionality of the odor body(ies) is most likely acetal and/or ketone, since sodium borohydride selectively eliminates these impurities.

Treatment with activate carbon appeared promising, selective for eliminating odor in the product. Different types of activated carbon were tested by the following procedure: in an 200 ml erlenmeyer flask, 0.5 grams of activated carbon was added to 50 grams of 1,3-butylene glycol. A 2 cm. stirring bar was added to the liquid and the mixture was stirred at 200 rpm for 12 hours at room temp. Stirring was terminated and the carbon is allowed to settle. An aliquot of the carbon treated material was removed from the flask and was submitted to an odor panel for evaluation along with a sample of untreated 1,3-butylene glycol.

Panel evaluation was carried out by a trained panel with the 1,3-butylene glycol having acceptable odor characteristics being assigned an odor value of 2 and 1,3-butylene glycol with superior characteristics being assigned a reference value of 1. Treated and untreated material was evaluated and assigned a panel odor value in 0.5 panel odor unit increments, that is, 0.5, 1, 1.5, 2, 2.5 and so forth. Different types of activated carbon were evaluated including a Calgon material (coal-based, believed to be steam activated), a Jacobi material (coconut shell-based, believed to be steam activated), and MeadWestvaco WVB-30 (sawdust-based, believed to be phosphorous acid activated) using the above procedures. The effectiveness of odor removal was sawdust>coal>coconut shell (Table III), with the coconut shell carbon treated material having an uncharacteristic, additional odor. All carbon types were tested using a constant weight per volume 1,3-butylene glycol, residence time, and mixing. Under optimum conditions, the MeadWestvaco activated carbon produced essentially odorless 1,3-butylene glycol at a weight ratio of 1:100 (carbon:1,3-butylene glycol).

TABLE III

Odor Panel Results

| Sample | Odor Rank | Overall Rank | Comments |
|---|---|---|---|
| 1 - Baseline | 2 | — | |
| 2 (Coconut Shell) | 1.4 | 3 | Reduced overall odor yet imparted a new, uncharacteristic odor. New odor is not part of our standard and was difficult to quantify. We assumed the new odor could actually increase the odor ranking. |
| 3 (Coal) | 1.2 | 2 | Reduced odor but had to use "dust" to get small enough particle size to reduce significantly. When used comparable mesh size, odor was reduced to 1.5 avg. The dust-like particles would be very hard to filter and be on test for color. |
| 4 (Sawdust, WVB-30) | 0.9 | 1 | Best overall odor reduction - some claimed "no odor" and there was no additional odors created. |

Fixed Bed Operation

A carbon tote was rented containing 660-lbs of MeadWestvaco activated carbon, Nuchar® WVB-30. The carbon was backflushed and left full of water for 24 hours to allow for degassing. Since the carbon was purchased wet and backflushed on site, it took approximately 2 hours to purge the water down to on-spec levels using 1,3-butylene glycol product residue. Despite filters there was some carbon fines breakthrough that needed to be resolved. A total of 204 Mlbs of 1,3-butylene glycol were processed through the carbon vessel. The treated 1,3-butylene glycol was analyzed for odor every 4 hours. The earliest production was found to have the least odor. As the test progressed, the odor gradually increased until it was apparent that the bed was approaching saturation and the trial was discontinued. Accumulated on-test material was analyzed after the termination of the trial and was found to have an odor of 1.0 while the starting material had an average odor of 2.0. Further analysis of the treated 1,3-butylene glycol showed no other quality impacts aside from reduced odor and color.

Economics

The 660 pounds of Nuchar® carbon was purchased at a price of $1.90/pound for a total of $1254. This carbon treated 204 Mlbs of 1,3-butylene glycol therefore the incremental cost for carbon treating was $0.0061/pound of 1,3-butylene glycol.

Fixed bed operation was scaled up to a larger bed. MeadWestvaco WB-30 material was charged to a fixed bed apparatus 10 shown schematically in FIG. 1. Apparatus 10 includes a vessel 12 for containing the activated carbon and is equipped with a loading line 14 for adding the activated carbon as well as a drain line 15 for removing material from vessel 12. A feed line 16 feeds 1,3-butylene glycol to vessel 12. A vent 18 and a relief valve 20 are also located as shown. A side draw 22 is provided for removing treated 1,3-butylene glycol from the bed and optionally filtration is placed on the bed outlet at 24 for sequestering fines and dust.

Prior to treating 1,3-butylene glycol, the WB-30 material was loaded to vessel 12 to provide a fixed bed 26 therein and de-gassed as described above. 1,3-butylene glycol was fed through line 16 to the fixed band at a rate of 1 bed volume per day and withdrawn at the same rate through side draw 22. The bed was operated over a period of months and the odor periodically evaluated as noted above. A total of more than 155 bed volumes of 1,3-butylene glycol was thus processed initially. In subsequent testing, 250-300 bed turnovers by volume were realized before the carbon was exhausted. The inventive process thus typically achieves odor reduction by one odor unit for at least 100 bed turnovers by volume, and preferably for at least 200-250 bed turnovers by volume.

Odor evaluation results for the material treated in apparatus 10 appear in FIG. 2, wherein it is seen the odor valves are typically 1-3 units lower than untreated material.

Perhaps more remarkably, the bed was still operating effectively to remove most of the odor after more than 155 bed volumes of 1,3-butylene glycol treated. The long service life suggests that the activated carbon may not only absorb odor-causing impurities, but may also operate to eliminate undesirable chemical species.

There is thus provided in one aspect of the invention a method of reducing odor of 1,3-butylene glycol comprising contacting the 1,3-butylene glycol with an activated carbon selected from wood-based activated carbons and chemically activated carbons. The activated carbon may be a chemically activated, wood-based activated carbon, activated by treatment with phosphoric acid. Preferably, the activated carbon employed is a granular activated carbon with one or more of the following characteristics: the granular activated carbon has a nominal particle size of from 6 mesh to 25 mesh; the activated carbon has an apparent density of from 200 kg/m³ to 350 kg/m³; and the activated carbon has a surface area of from 1000 m²g to 2000 m²/g.

Alternatively, the activated carbon is pelletized activated carbon and has a pellet diameter of from 2 mm to 6 mm.

Generally, the activated carbon has an iodine number of at least 900 mg/g and the 1,3-butylene glycol treated is produced by aldol combination of acetaldehyde.

Typically, the treatment with activated carbon is effective to reduce the level of ketone or acetal impurities in the 1,3-butylene glycol treated.

In another aspect of the invention, there is provided a method of reducing odor of 1,3-butylene glycol comprising contacting the 1,3-butylene glycol with a fixed bed of particulate activate carbon material selected from wood-based activated carbon and chemically activated carbons for a residence time of 1,3-butylene glycol in the bed of from 1 hour to 48 hours. Generally, the residence time of 1,3-butylene glycol in the bed is from 6 hours to 36 hours with from 12 hours to 30 hours typical. In some particular embodiments, the residence time of 1,3-butylene glycol in the bed is from 18 hours to 24 hours. Usually, the process includes de-gassing the activated carbon prior to contacting the activated carbon with the 1,3-butylene glycol to be purified by way of, for example, flushing the fixed bed of activated carbon with water. The fixed bed is optionally left full of water for at least 12 hours to de-gas the activated carbon.

In another aspect of the invention a method of post-treating a finished 1,3-butylene glycol to reduce odor consists of contacting the 1,3-butylene glycol with an activated carbon material selected from wood-based activated carbon and chemically activated carbons, wherein the 1,3-butylene glycol is consumed without further purification.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A method of reducing odor of 1,3-butylene glycol comprising contacting the 1,3-butylene glycol with an activated carbon selected from wood-based activated carbons and chemically activated carbons.

2. The method according to claim 1, wherein the activated carbon is a wood-based activated carbon.

3. The method according to claim 2, wherein the activated carbon is a chemically activated, wood-based activated carbon.

4. The method according to claim 3, wherein the wood-based activated carbon is activated by treatment with phosphoric acid.

5. The method according to claim 1, wherein the activated carbon employed is a granular activated carbon.

6. The method according to claim 5, wherein the granular activated carbon has a nominal particle size of from 6 mesh to 25 mesh.

7. The method according to claim 1, wherein the activated carbon has an apparent density of from 200 kg/m$^3$ to 350 kg/m$^3$.

8. The method according to claim 1, wherein the activated carbon has a surface area of from 1000 m$^2$g to 2000 m$^2$/g.

9. The method of claim 1, wherein the activated carbon is pelletized activated carbon having a pellet diameter of from 2 mm to 6 mm.

10. The method according to claim 1, wherein the activated carbon has an iodine number of at least 900 mg/g.

11. The method according to claim 1, wherein the 1,3-butylene glycol treated is produced by aldol combination of acetaldehyde.

12. The method according to claim 1, effective to reduce the level of ketone or acetal impurities in the 1,3-butylene glycol treated.

13. A method of reducing odor of 1,3-butylene glycol comprising contacting the 1,3-butylene glycol with a fixed bed of particulate activate carbon material selected from wood-based activated carbon and chemically activated carbons for a residence time of 1,3-butylene glycol in the bed of from 1 hour to 48 hours.

14. The method according to claim 13, wherein the residence time of 1,3-butylene glycol in the bed is from 6 hours to 36 hours.

15. The method according to claim 13, wherein the residence time of 1,3-butylene glycol in the bed is from 12 hours to 30 hours.

16. The method according to claim 13, wherein the residence time of 1,3-butylene glycol in the bed is from 18 hours to 24 hours.

17. The method according to claim 13, further comprising de-gassing the activated carbon prior to contacting the activated carbon with the 1,3-butylene glycol to be purified.

18. The method according to claim 17, wherein the step of de-gassing the activated carbon comprises flushing the fixed bed of activated carbon with water.

19. The method according to claim 18, wherein the fixed bed is left full of water for at least 12 hours to de-gas the activated carbon.

20. A method of post-treating a finished 1-3-butylene glycol to reduce odor consisting of contacting the 1,3-butylene glycol with an activated carbon material selected from wood-based activated carbon and chemically activated carbons, wherein the 1,3-butylene glycol is consumed without further purification.

* * * * *